US006253097B1

United States Patent
Aronow et al.

(10) Patent No.: US 6,253,097 B1
(45) Date of Patent: *Jun. 26, 2001

(54) NONINVASIVE MEDICAL MONITORING INSTRUMENT USING SURFACE EMITTING LASER DEVICES

(75) Inventors: Kurt A. Aronow, Lafayette; Jonas A. Pologe, Boulder, both of CO (US)

(73) Assignee: Datex-Ohmeda, Inc., Tewksbury, MA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/612,628

(22) Filed: Mar. 6, 1996

(51) Int. Cl.[7] .......................................... A61B 5/00
(52) U.S. Cl. ............................... 600/310; 600/323
(58) Field of Search ........................... 128/633, 664–667; 372/45–52; 600/310, 322–324, 326, 336, 341

(56) References Cited

U.S. PATENT DOCUMENTS

| 4,167,331 | * | 9/1979 | Nielsen . | |
|---|---|---|---|---|
| 4,663,913 | * | 5/1987 | L'Esperance, Jr. | 606/5 |
| 4,669,466 | * | 6/1987 | L'Esperance | 606/5 |
| 4,732,148 | * | 3/1988 | L'Esperance, Jr. | 606/5 |
| 5,068,869 | * | 11/1991 | Wang et al. | 372/45 |
| 5,070,509 | * | 12/1991 | Meyers | 372/45 |
| 5,209,230 | * | 5/1993 | Swedlow et al. | 128/664 |
| 5,284,477 | * | 2/1994 | Hanna et al. | 606/5 |
| 5,313,940 | * | 5/1994 | Fuse et al. | 128/633 |
| 5,339,810 | * | 8/1994 | Ivers et al. | 128/664 |
| 5,357,953 | * | 10/1994 | Merrick et al. | 128/633 |
| 5,368,025 | * | 11/1994 | Young et al. | 128/633 |
| 5,480,396 | * | 1/1996 | Simon et al. | 606/4 |
| 5,511,546 | * | 4/1996 | Hon | 128/633 |
| 5,645,550 | * | 7/1997 | Hohla | 606/108 |
| 6,026,312 | * | 2/2000 | Shemwell et al. | 600/310 |

OTHER PUBLICATIONS

Powers, "An Intro to Fiber Optic Systems," Aksen Associates. Boston, MA, 1993, p. 123.*

* cited by examiner

Primary Examiner—Linda C. M. Dvorak
Assistant Examiner—Roy Gibson
(74) Attorney, Agent, or Firm—Marsh Fischmann & Breyfogle LLP (57) ABSTRACT

A medical monitoring instrument such as a pulse oximeter uses vertical cavity surface emitting laser diodes (VCSELs) to produce at least two high intensity, essentially monochromatic light beams. The VCSELs are located either in: (1) the probe itself, (2) the connector to the probe, or (3) the monitor box connected with an optical fiber to the probe.

20 Claims, 10 Drawing Sheets

NONINVASIVE MEDICAL MONITORING INSTRUMENT USING SURFACE EMITTING LASER DEVICES

CROSS REFERENCE TO RELATED APPLICATIONS

This application is related to U.S. patent application Ser. No. 08/458,485 titled "Instrumented Laser Diode Probe Connector", filed Jun. 2, 1995.

FIELD OF THE INVENTION

This invention is in the field of medical monitoring instruments such as pulse oximeters. The invention uses vertical cavity surface emitting laser diodes (VCSELs) as the light sources. The VCSELs are located either in: (1) the probe itself, (2) the connector to the probe, or (3) the monitor box connected with an optical fiber to the probe.

PROBLEM

It is a problem in the field of medical monitoring instruments to manufacture a monitoring instrument that satisfies a number of diverse and sometimes contradictory requirements. It is important that the monitoring instrument be simple to use, in that it conforms to a variety of patients who differ in size and shape. The probe must be securely affixable to the patient, such as on a patient's appendage, without requiring complex structures or elements that can irritate the patient. In addition, in order to reduce the risk of infection and contamination, the probe is built to be disposable so that the probe is used one or more times with the patient and then destroyed. In some cases the probe must also be inexpensive so that it can be disposable after use and yet the patient must be shielded from any potentially dangerous electrical signals or heat produced by the probe. The probe must also reliably and accurately perform the required measurements. The probe, cable and monitoring instrument are all subject to a hostile operating environment and must be manufactured to be rugged to survive rough handling and the presence of highly reactive fluids. The probe must therefore maintain the required measurement accuracy, be rugged to withstand the hostile environment, be safe for attachment to the patient and yet be inexpensive since it is often a disposable element. To achieve these goals, compromises are typically made, although the accuracy of the measurements tends to be of paramount importance.

In the specific field of photoplethysmography, the light beams that are generated by the probe must be of sufficient intensity to illuminate the perfused tissue and also be of constant wavelength, since the light absorption of the monitored analyte varies as a function of wavelength. Light emitting diodes (LEDs) that produce light beams at red and infrared wavelengths are typically used in the probe for this purpose. The production of an intense beam of light must be balanced with the requirement that the probe does not operate at a significantly elevated temperature, which would cause irritation to the patient's skin. A complicating factor is that the light emitting diodes are mounted in the probe module, and are juxtaposed to the patient's skin. The light emitting diodes are therefore subject to significant temperature fluctuations and the corresponding changes in wavelength output by the light emitting diodes, which causes a measurable source of error in the measurements that are taken by the monitor device.

It is preferable in photoplethysmographic systems to use laser diodes, which produce a beam of substantially monochromatic light similar to or exceeding the light power available from light emitting diodes that are typically used in photoplethysmography. The difficulty with laser diodes currently available is that their cost prevents them from being used in a disposable probe. Placement of the laser diode in the monitoring instrument necessitates the use of one or more fiber optic strands in the cable that interconnects the disposable probe with the monitoring instrument. The cable in a hospital environment typically suffers rough handling and the life of the fiber optic strands in the connector cable can be fairly limited, thereby increasing the effective cost of the disposable probe since the cable must be replaced on a fairly frequent basis.

Thus, there presently does not exist a monitoring instrument that can fully satisfy this plurality of diverse requirements in a manner that does not compromise the performance of the monitoring instrument.

SOLUTION

The above describe problems resolved and a technical advance achieved in the field of medical monitoring instruments by the apparatus of the present invention which makes use of a monochromatic light source, in the form of a plurality of surface emitting laser devices, to produce a plurality of high intensity substantially monochromatic beams of light. In the preferred embodiment of the invention disclosed herein, the monitoring instrument and probe comprise an arterial blood monitoring instrument, such as a pulse oximeter instrument which noninvasively monitors blood analytes in the patient. The use of monochromatic light improves the accuracy of the measurements and simplifies the calibration process.

The light source is an array of surface emitting laser devices, each of which outputs a substantially monochromatic beam of light of substantially circular cross section. The preferred embodiment of this apparatus places the laser diodes in the connector at the distal end of the cable proximate to the disposable portion of the probe to thereby implement an instrumented connectorized laser diode probe cable. Placement of the light source at the point of contact on the patient and using surface emitting laser devices, the light beam can directly irradiate the perfused tissue and the probe can be constructed to be more lightweight, conformable and inexpensive. This architecture eliminates the need for fiber optic strands in the cable yet provides the benefits of laser diode light generation over the presently used light emitting diodes. Furthermore, the potentially disposable section of the probe can be a minimalistic design since all the expensive active elements are located in the cable connector. The disposable section of the probe simply consists of the apparatus required to affix the probe to the patient's appendage and the mating portion of the connector that interconnects with the cable and a photodetector. An alternative embodiment of the invention places the surface emitting laser diodes in the probe itself, rather than in the connector, thereby simplifying the connector implementation and making the surface emitting laser diodes an integral element in the probe. Another alternative embodiment of the invention places the surface emitting laser diodes in the monitoring instrument itself and transmits the generated beams of light to the potentially disposable segment of the probe via a cable.

This basic probe architecture with the light source detached from the probe, and using surface emitting laser diodes, overcomes the problems inherent in existing probes and also is architected for ease of reliable and accurate manufacture. The probe generates a constrained light path, can be less expensive than existing probes and uses improved packaging with fewer conductors required to connect the probe with the monitor. This monitor and probe architecture therefore represents a significant advance in the technology of medical monitoring instruments.

DETAILED DESCRIPTION

Figure 1:
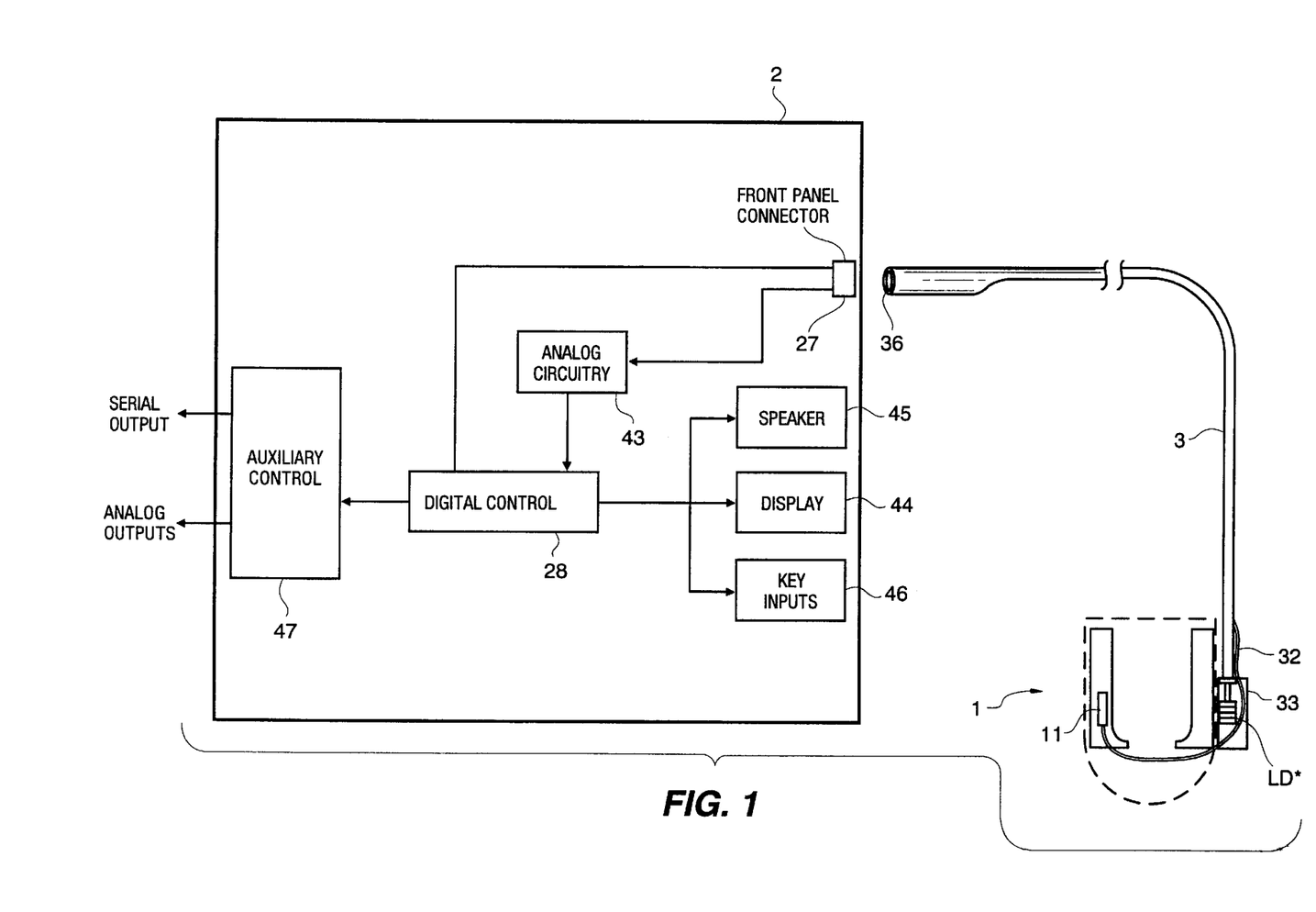
FIG. 1 illustrates the architecture of probe of the preferred embodiment of the present invention, including a side cutaway view of the probe and a block diagram of the control elements of the monitor.

Any improvements, however incremental, in the design and manufacturability of a probe in the field of medical monitoring instruments result in significant cost savings. The apparatus of the preferred embodiment of the present invention consists of two segments: a monitor comprising the electronics which include the control and display circuitry, and a probe that is affixed to a probe attachment site on the patient. FIG. 1 illustrates the probe in side cutaway view and a block diagram of a portion of the elements that comprise the monitor. FIGS. 2–5, 7–9, and 12–13 illustrate details of alternative probe and system implementations.

Photoplethysmographic Probe Application

A pulse oximeter instrument is frequently used to monitor the condition of a patient in a hospital setting. The pulse oximeter instrument noninvasively measures the oxygen saturation of the arterial blood and produces a human readable display that indicates both the patient's heart rate and the oxygen saturation of the arterial blood. These readings are important to enable the medical staff to determine whether the patient'respiratory system is functioning properly, supplying sufficient oxygen to the blood.

A pulse oximeter instrument operates by use of a probe that illuminates an appendage of the patient (such as a finger, earlobe, or the nasal septum) that is rich in arterial blood and measures the differential absorption of the light by the pulsatile portion of the arterial blood flow to thereby determine the oxygen saturation of the arterial blood. The pulse oximeter instrument makes use of a plurality of light-emitting devices, each of which emits light with a predetermined spectral content The emitters are selected such that their spectral contents, and their position on the extinction curves, will provide the most unique mapping from the absorption measurements to the calculated analyte levels. The amount of absorption of the light beams generated by these light emitting devices that are located in the probe is a measure of the relative concentration of the oxygenated and reduced hemoglobin (as well as the other selected hemoglobin species) in the arterial blood. The absorption of the light that illuminates the appendage of the patient includes a constant portion that is a result of skin, bone, steady-state (venous) blood flow and light loss due to various other factors. The pulsatile component of absorption is due to the pulsatile arterial blood flow, is a small fraction of the received signal and is used by the pulse oximeter instrument to perform its measurements. It is also possible to measure additional analytes in the arterial blood, such as additional dyshemoglobins (MetHb and COHb), with at least one additional wavelength of light for each analyte. Monochromatic light sources are desirable for all the emitters to avoid overlap of the spectral content of the emitters and to provide precise positioning of the spectral content of each emitter with respect to the hemoglobin extinction curves.

The measurements are computed by sampling the output of the light detector located in the probe to determine the incremental changes in absorption of the light from the various emitters that are used to illuminate the appendage of the patient. These incremental changes in light absorption are then used to compute the oxygen saturation of the arterial blood, the relative concentration of other selected hemoglobin species, as well as the patient's pulse rate. Since the pulsatile component of the signals received by the light detector represent only a small fraction of the received light, it is important that the incident light be of significant magnitude to result in transmitted signals that have sufficient amplitude to provide accurate readings. In addition, the probe containing the light-emitting devices and the light detector must be placed in intimate contact with the skin of the patient to obtain the most accurate readings. The probe design must therefore be such that it inherently accommodates variations in size and shape of the patient's appendage and also enables the medical staff to simply apply the probe to obtain the optimum readings. These stringent requirements are difficult for existing probes to comply with and increase the manufacturing cost of the probes, which may include disposable elements.

Figure 6:
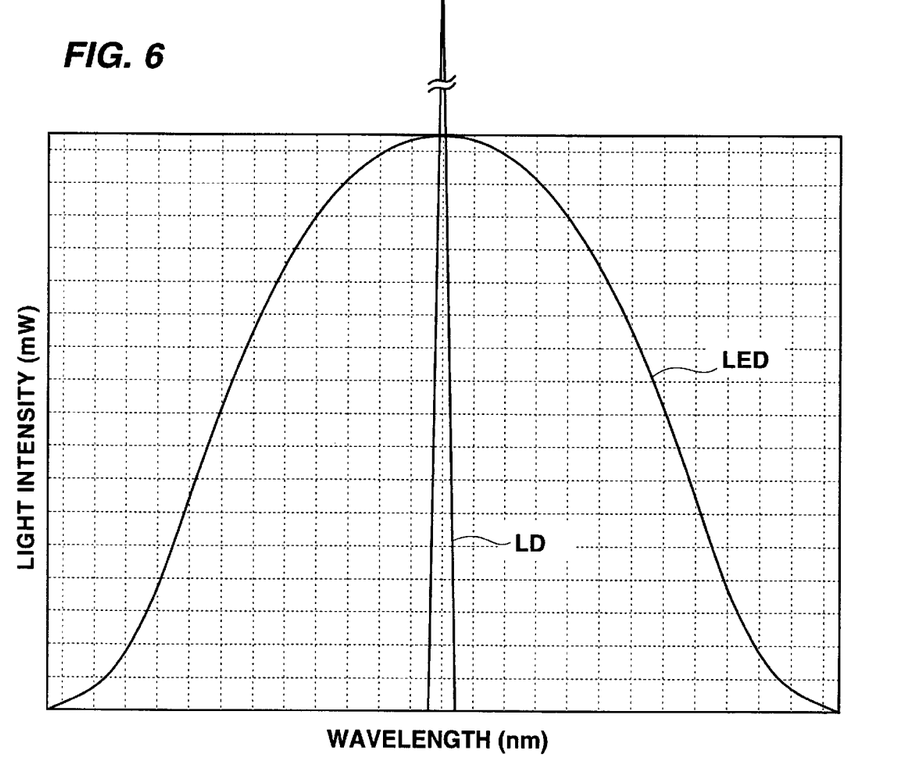
FIG. 6 illustrates a waveform of the comparative light output of laser diodes and light emitting diodes.

Probe Philosophy The term "probe", as used herein, is defined to include the apparatus which affixes the probe to the patient, as well as the electronic devices used to perform the sensor function. Associated with the electronic devices are signal conductors and typically one or more connectors to interconnect the probe with the monitor. The light emitting devices used in the photoplethysmographic (pulse oximeter) instrument application disclosed herein are surface emitting laser devices, which produce an intense conic beam of light that is substantially monochromatic. The selection of surface emitting laser devices to generate the light beams that are used to illuminate the perfused tissue of the patient is a result of the preferable output characteristics of the laser device as compared to the light emitting diode. FIG. 6 illustrates the spectral content of these respective devices, with the laser device producing a beam of light, whose spectral content (LD) is centered about a selected wavelength, such as 660 nm, and having a bandwidth of as little as 1 nm. The light emitting diode produces a beam of light whose spectral content (LED) is centered about a selected wavelength, such as 660 nm, and having a bandwidth of 60 nm in width or greater. Thus, the laser device is able to generate a great deal of power over a narrow spectral range when compared to a light emitting diode.

In addition to the extent of the bandwidth, the variations in bandwidth and shape of the spectral output curve among light emitting diodes represent a significant problem. The tail end of the spectral emissions of the light emitting diode can have a measurable effect on the received signal from the perfused tissue. The magnitude and extent of the tail portion of the spectral emissions is more difficult to measure and account for than the signal output at maximum intensity. A complicating factor is that the light emitting diodes are mounted in the probe module, and are juxtaposed to the patient's skin. The light emitting diodes are therefore subject to significant temperature fluctuations and the corresponding changes in wavelength output by the light emitting diodes, which cause a measurable source of error. Finally, another source of error is the "venous prefiltering", wherein the spectral output of the light emitting diodes is unevenly and unpredictably attenuated across the span of generated wavelengths by the presence of the venous and non-pulsatile arterial components of the blood. This attenuation of the light is a function of the oxygen saturation of the blood and wavelength, varies from subject to subject, and also is temporal in nature, varying within a given patient. The arterial blood flow is highly variable in the extremities of a patient, where the pulse oximetry readings are taken. The difference in oxygen saturation between arterial and venous components of the blood can be from as little as less than one percent to greater than twenty-five percent. Thus, the greater the spectral bandwidth, potentially the greater this source of error. Sources of error are inherent in the light emitting diode and the method of placing the light emitting diode on the patient's appendage to perform readings. There is no accurate way to quantify or compensate for the sources of error.

Vertical Cavity Surface Emitting Laser Devices

Figure 10:
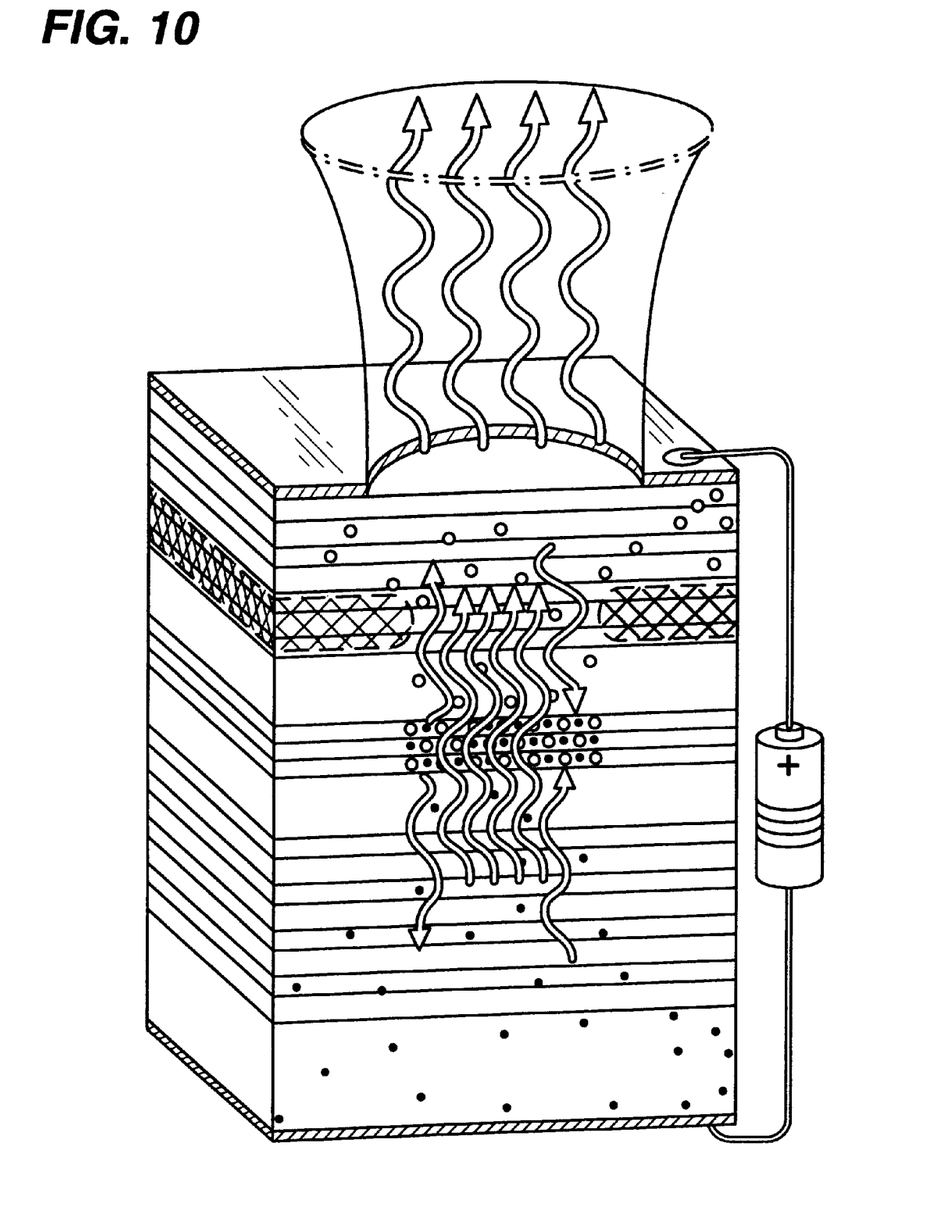
FIG. 10 illustrates an illustrative cross-section view of a surface emitting laser device.

A vertical cavity surface emitting laser, as illustrated in cross-section view in FIG. 10, is a solid state surface emitting laser device in which two mirrors as well as the intervening gain region are grown epitaxially on a semiconductor substrate. Light generated in the gain region bounces vertically between the mirrors and some leaks through the top surface mirror in a direction normal to the top surface to form the emitted beam of light Laser devices that emit light from their upper surface can be fabricated side by side on a wafer (in an array pattern) and also integrated with other solid state devices on a single chip. Coupling efficiency also benefits from a surface emitting geometry. The beam of light that issues from a traditional edge emitting laser device is usually both elliptical and divergent, with the angle of divergence of the beam of light for the large angle of the ellipse typically being 30° off the normal, which can result in low coupling efficiency (into a fiber). In contrast, the surface emitting laser device uses a shaped aperture to provide a more constrained light path which results in a beam of circular cross section and of sufficient diameter to make the beam generally less divergent than the beam of light which is generated by edge emitting laser devices, with the angle of divergence typically being approximately 10° off the normal for the surface emitting laser device, which results in much greater efficiency than one typically possible with edge emitting laser diodes.

Figure 11:
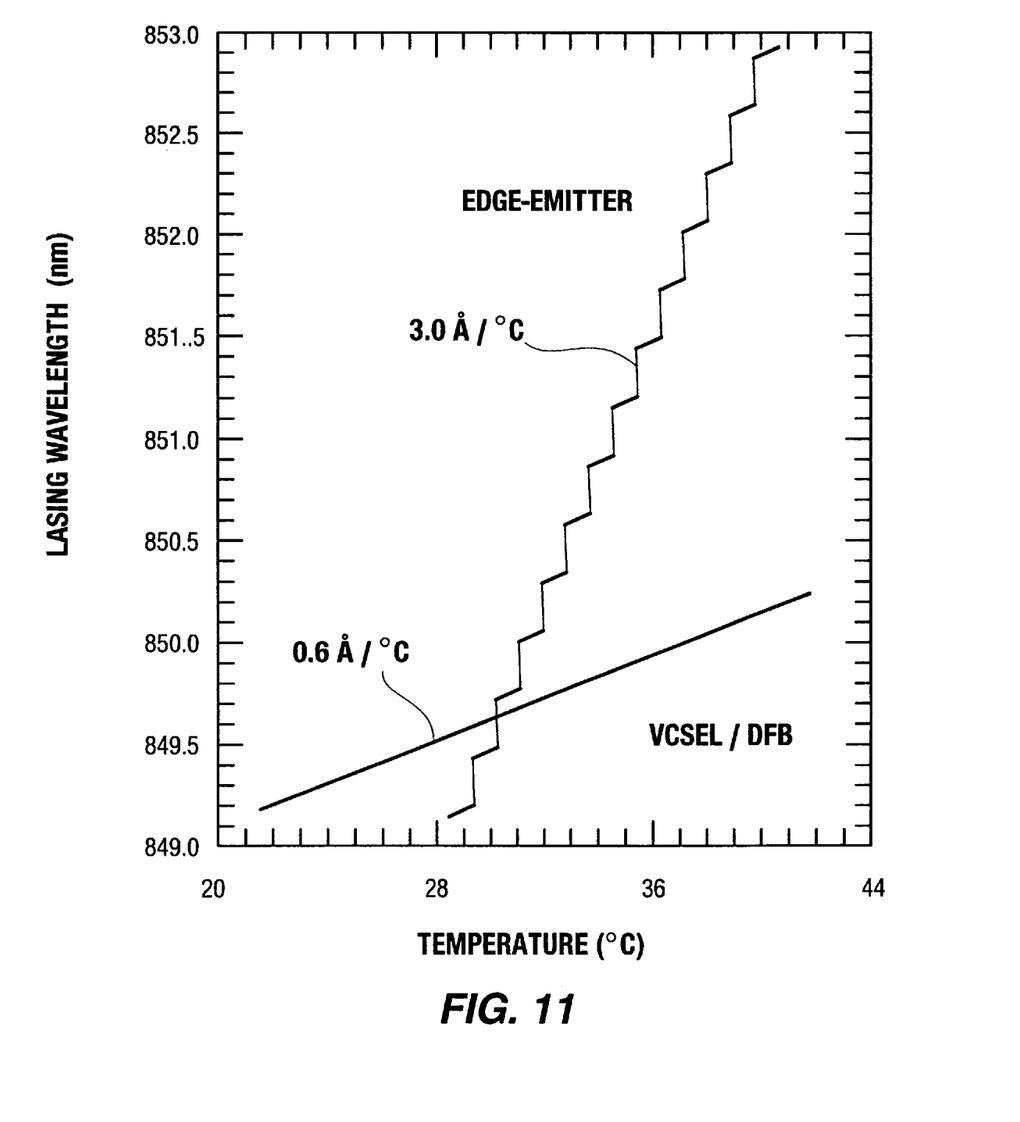
FIG. 11 illustrates a waveform illustrative of typical operating characteristics of edge emitting laser diodes.

The surface emitting laser diodes have advantages over the edge emitting laser diodes in that their operating characteristics are more stable. In particular, FIG. 11 illustrates a graph of the respective temperature characteristics of edge emitting laser diodes and surface emitting laser diodes. As can be seen from this graph, the edge emitting laser diode has a much steeper curve of lasing wavelength as a function of temperature than the surface emitting laser diode. In addition, the operating curve of the edge emitting laser diode is discontinuous because the edge emitting laser diode is subject to mode hopping, which is a stepwise transition to a different cavity resonance. This mode hopping causes calibration problems and typically requires stringent temperature control or compensation of the operating temperature of the edge emitting laser diode.

There are a number of additional benefits to using surface emitting laser diodes. The surface emitting laser diodes can be tested in situ on the wafer on which they are fabricated, while the edge emitting laser diodes must be sliced from the wafer, wire bonded to leads and then tested. The reduction in the cost and complexity of the device screening process represents a significant advantage to the use of surface emitting laser diodes. Furthermore, the surface emitting laser diodes can be mounted in an array or excised from the wafer in an array having a small cross-section which enables the use of additional surface emitting laser diodes to thereby provide the correct number of wavelengths, or an overdetermined system and/or redundant devices at a smaller additional cost compared to the use of individual laser devices which are fabricated on separate devices. Finally, the cross-section of the light beam output by the surface emitting laser diodes is round and thereby mates more efficiently with the optical fiber which can be used as the light transmission medium. Generally, no lenses (or simple lenses) need to be used to couple the light output of the surface emitting laser diode into the optical fiber.

Probe Architecture

The apparatus of the preferred embodiment of the present invention, as illustrated in block diagram form in FIG. 1, consists of two primary segments: a monitor 2, and a probe 1 that is affixed to a probe attachment site on the patient. These two modules 1, 2 are interconnected by a cable 3 which can be affixedly attached to and an integral part of probe 1 or can be an element that is connectorized at both ends thereof to enable cable 3 to be disconnected from both the probe 1 and monitor 2. In the preferred embodiment disclosed herein, the cable 3 is shown as interconnected with the probe 1 via a connector. The light emitting devices are preferably mounted within this connector so that the apparatus which functions to affix the probe 1 to the patient can be disconnected from the apparatus which contains the light emitting devices.

Monitor

The monitor 2 includes circuitry to receive the return signals produced by the reception of light that passes through the illuminated appendage as well as user interface circuitry. The monitor 2 includes analog circuitry 43 which functions to receive and condition the electrical signals produced by the light detector 11 that is contained within the probe 1, as is well known in the art These received signals are digitized and transmitted to digital control 28 for processing as is well known in the field to produce the required measurements. The digital control 28 outputs the computed measurements to display 44 for production of a human-readable output.

A speaker 45 is typically included in monitor 2 to enable digital control 28 to produce audible alarms to alert the user to error or danger conditions. Key inputs 46 are also typically provided to enable the user to input control information to regulate the operation of the instrument. An auxiliary control circuit 47 receives output signals from digital control 28 for transmission in serial digital and/or analog form to other elements in the medical monitoring instrument.

Cable Connector The cable connector 33 consists of the light generation apparatus (laser diodes LD*), conductor 32 to connect to the light detector 11 in probe 1 and optical apparatus that applies the light beams generated by the laser diodes to the patient's appendage. A plurality of laser diodes (such as an array of surface emitting laser diodes) are noted in FIG. 1, labeled as "LD*". The number of laser diodes LD* is equal to or greater than the number of blood analytes that are to be measured by the instrument For standard pulse oximetry, the number of laser diodes can be as little as two, one whose light output is at a wavelength of approximately 660 nm and a second whose light output is at a wavelength of approximately 940 nm. In the system disclosed herein, four laser diodes LD* are disclosed. The wavelength of the light beams output by the laser diodes LD* are effected by the operating temperature of the laser diodes LD*. This configuration allows the light generated by the laser diodes LD* in the cable connector 33 to be output therefrom in a cone shaped pattern, whose symmetric axis is substantially perpendicular to the patient's skin, so while the generated light is incident on the patient's skin, the laser diodes LD* are not in intimate contact with the patient's skin. A diffuser may be added to the cable connector 33 so that the emitted laser light is not as dangerous to the user if the user looks directly at the laser light.

Probe Cable Connector Implementation Details

Figure 7:
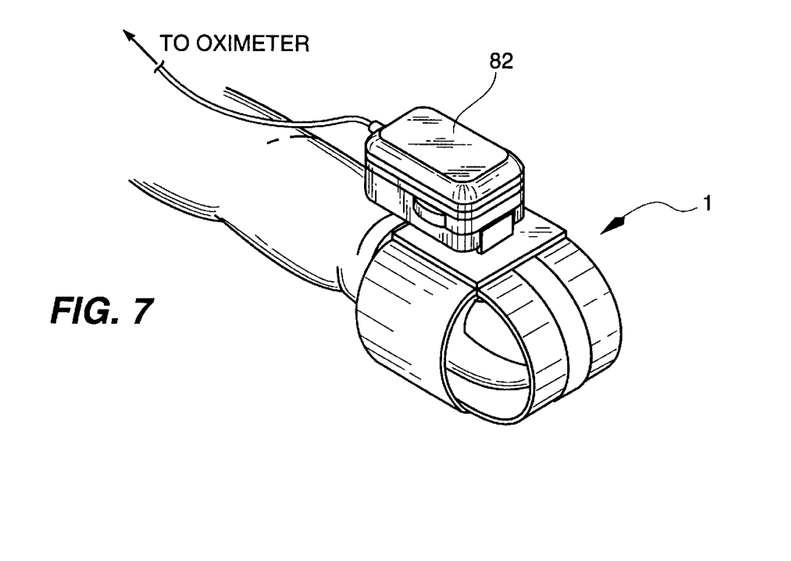
Figure 8:
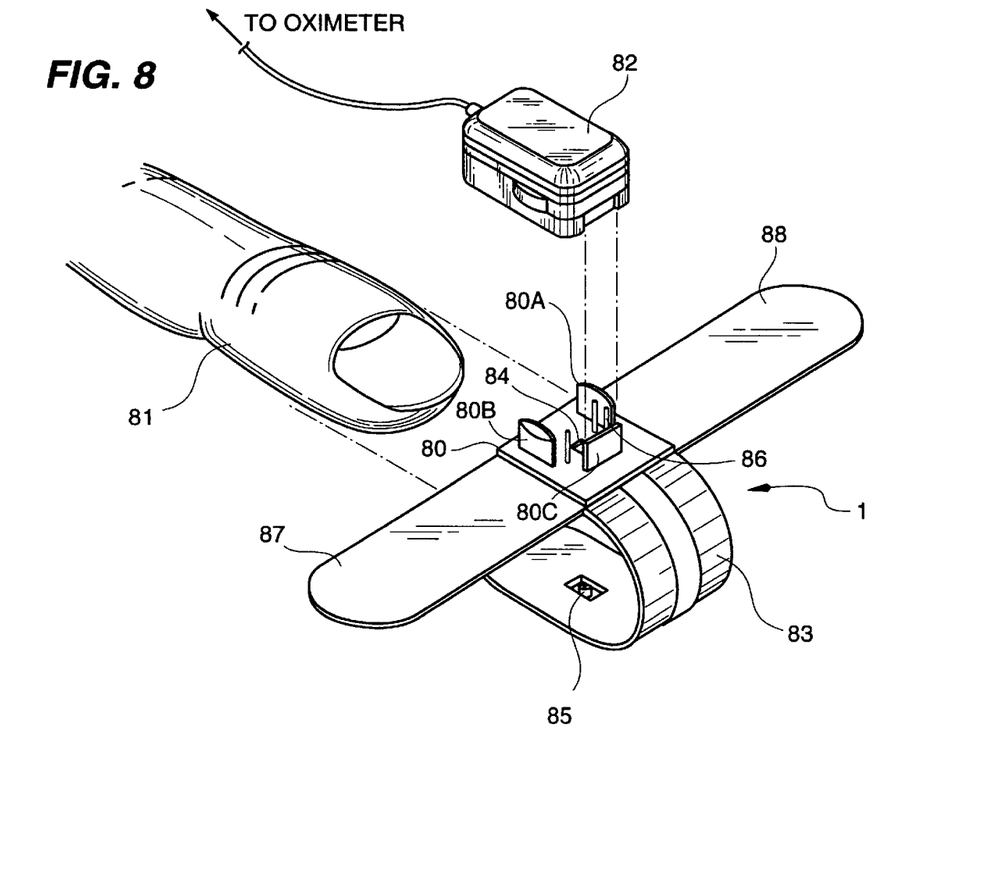
FIGS. 8 and 9 illustrate an alternative embodiment of the probe.

The implementation details of the preferred embodiment of the cable connector of the present invention are disclosed in additional detail in FIGS. 4, 5, 7–9. FIGS. 7 and 8 illustrate the probe 1 and cable connector 82, (which contains the laser diodes) interconnected together (FIG. 7) and separated into the individual parts (FIG. 8). The probe of FIG. 8 comprises a bandage type of disposable segment implementation, wherein connector segment 80 interconnects light detector 85 and optical port 84 with cable connector 82. A plurality of projections 80A, 80B, 80C serve to align cable connector 82 with pins 86 of connector 80 and securely affix cable connector 82 with connector 80, as described below. Flexible segment 83 wraps around the tip of the patient's finger 81 as shown in FIG. 7 and the probe 1 is securely held in place on the patient's finger by adhesive strips 87, 88 in well known manner.

Figure 4:
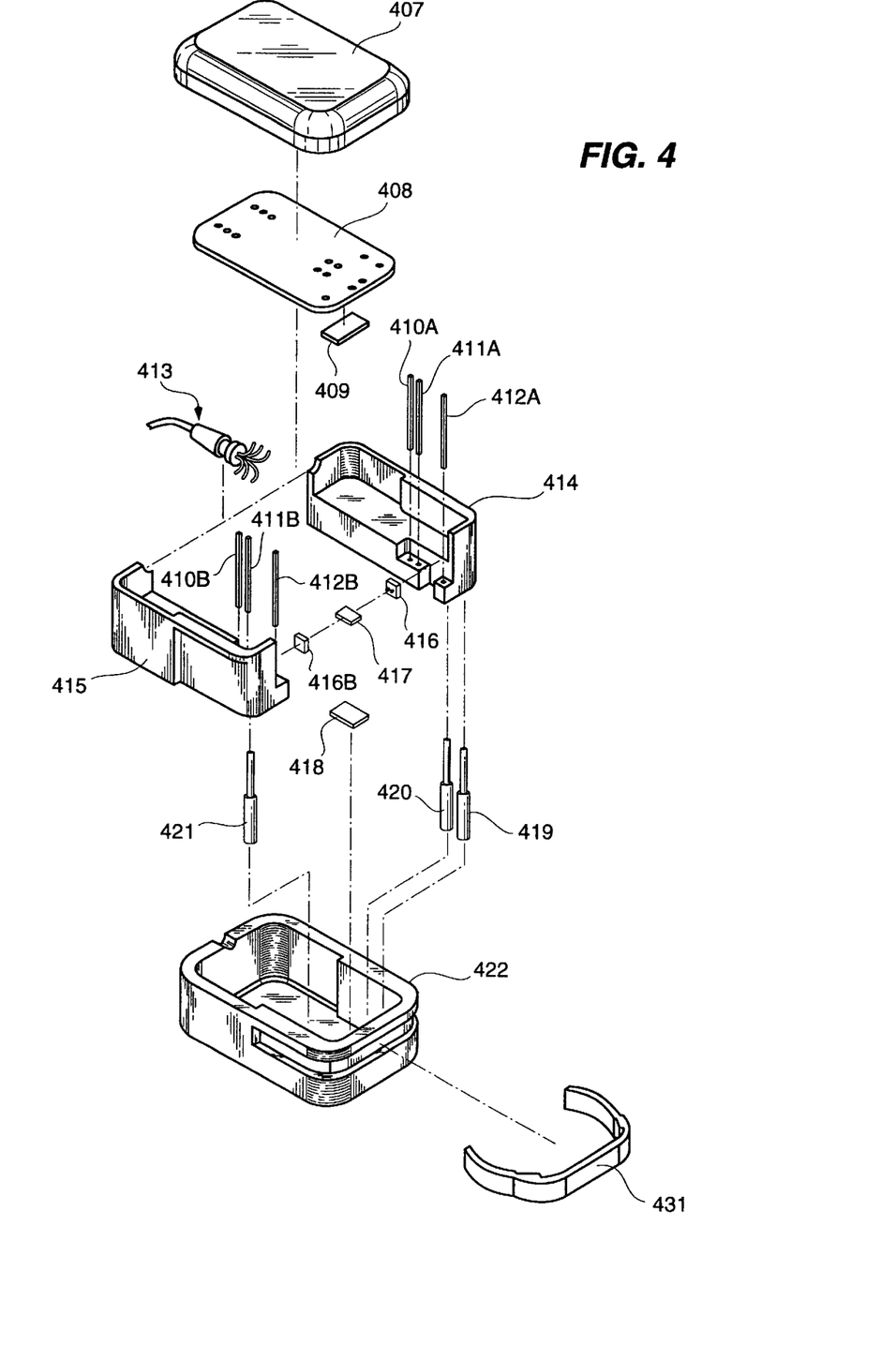
FIGS. 4, 5 and 7 illustrate top isometric (exploded), bottom isometric (exploded) and perspective views, respectively of the cable connector.
Figure 5:
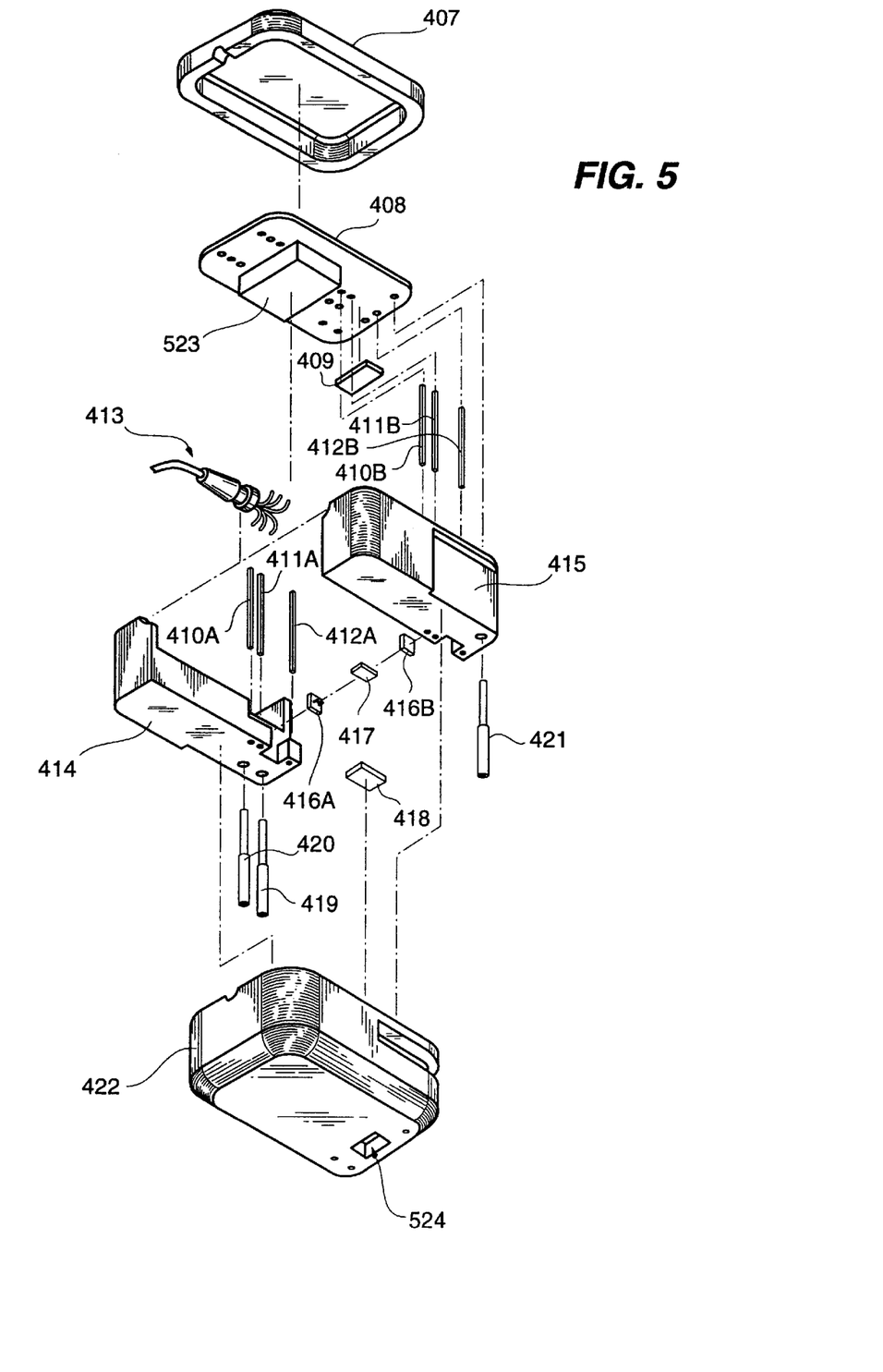

FIGS. 4 and 5 illustrate top isometric and bottom isometric exploded views, respectively, of the cable connector 82. This cable connector 82 comprises a housing 422 that is equipped with cover 407 to enclose and protect the remaining elements from the ambient environment. Included in cable connector 82 is a pair of heat sinks 414, 415 which serve to maintain the plurality of laser diodes 416A, 416B at a moderate operating temperature. The heat sinks 414, 415 seat within housing 422 and may be thermally interconnected via a coating of thermally conductive paste applied to the mating surfaces thereof. Heat sinks 414, 415, when installed in housing 422, provide a shelf on which circuit board 408 rests. The circuit board 408 contains circuit element 523 which provides at least some of the analog and digital circuitry that is used to interface with the laser diodes 416A, 416B and light detector 11. The circuit board 408 may partly or largely obviate the need for the analog circuitry 43 illustrated on FIG. 1. Photodetector 409 is also mounted on circuit board 408 and functions, in conjunction with circuit element 523 to regulate the output of laser diodes 416A, 416B. Cable 3 is terminated on circuit board 408 via strain relief 413, which also provides an environmental seal as it passes through a corresponding opening in housing 422. A plurality of connector sockets 419–421 pass through and are aligned by insulated holes in heat sinks 414, 415 to connect to circuit board 408 and the circuit element 523. The connector sockets 419–421 function as the conductors that interconnect cable connector 82 with corresponding connector pins 86 on probe connector 80. Spring clip 431 functions to secure the cable connector 82 with probe connector 80 when the two elements are physically interconnected as shown in FIG. 7. The projections 80A, 80B fit into mating holes on the bottom of housing 422 and snap fit with spring clip 431 as they pass through these holes. A user can thereby disconnect the cable connector 82 from probe connector 80 by simply applying force to the exposed section of spring clip 431 to deflect projections 80A and 80B a sufficient distance to clear the edges of the holes in the bottom of housing 422.

Figure 9:
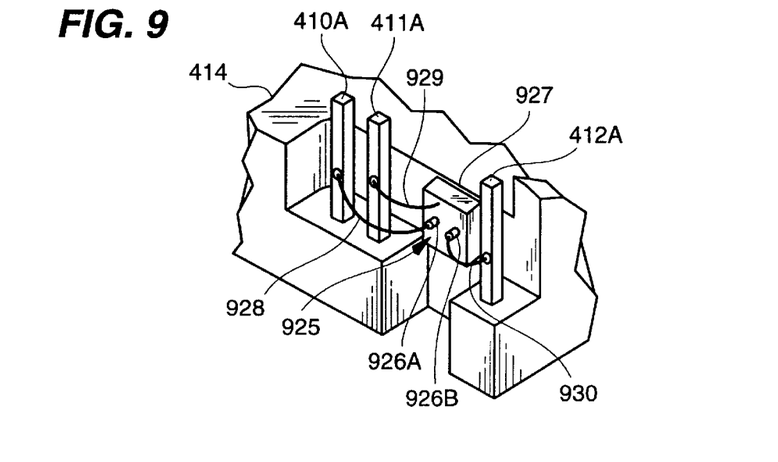

FIG. 9 illustrates additional details of the laser diode installation in cable connector 82. The four laser diodes are installed in two pairs 416A, 416B, with each pair of laser diodes being mounted via substrate base 925 and thermally conductive bonding agent 927 on a corresponding heat sink 414, 415 for thermal dissipation. Three pins 410A, 411A, 412A are installed in heat sink 414 to provide conductors to which the terminals of laser diodes 926A, 926B are connected. Conductor 411A is electrically connected to heat sink 414 and to laser diodes 926A, 926B via conductor 929. Pins 410A and 412A are electrically insulated from heat sink 414 and function to interconnect the laser diodes 926A, 926B with circuit board 408. Conductors 928 and 930 function to connect laser diodes 926A, 926B to pins 410A, 412A. The light output of laser diodes 926A, 926B is carried through window 418 through opening 524 in housing 422. Window 418 may be clear or at least partially diffusing to prevent damage to a user's eye if the user were to look directly into the beam of light generated by the laser diodes 926A, 926B and exiting the cable connector 82. An opaque shade 417 is provided to prevent optical transmission of ambient light from opening 524 to photodiode 409.

Alternative Probe Implementations

Figure 2:
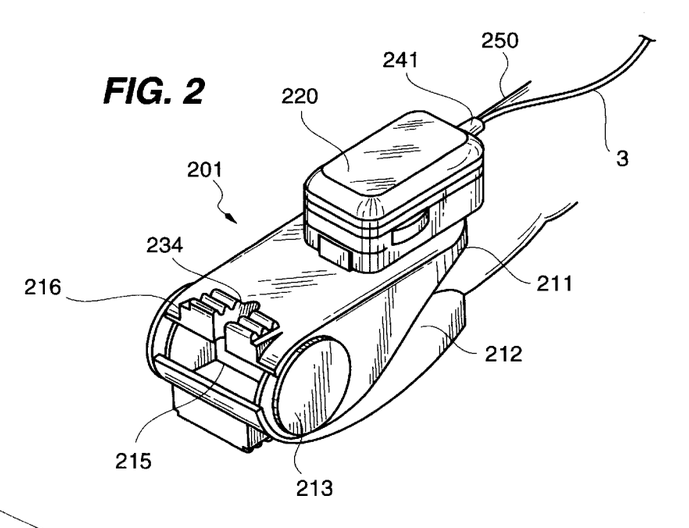
FIGS. 2 and 3 illustrate one implementation of the probe.
Figure 3:
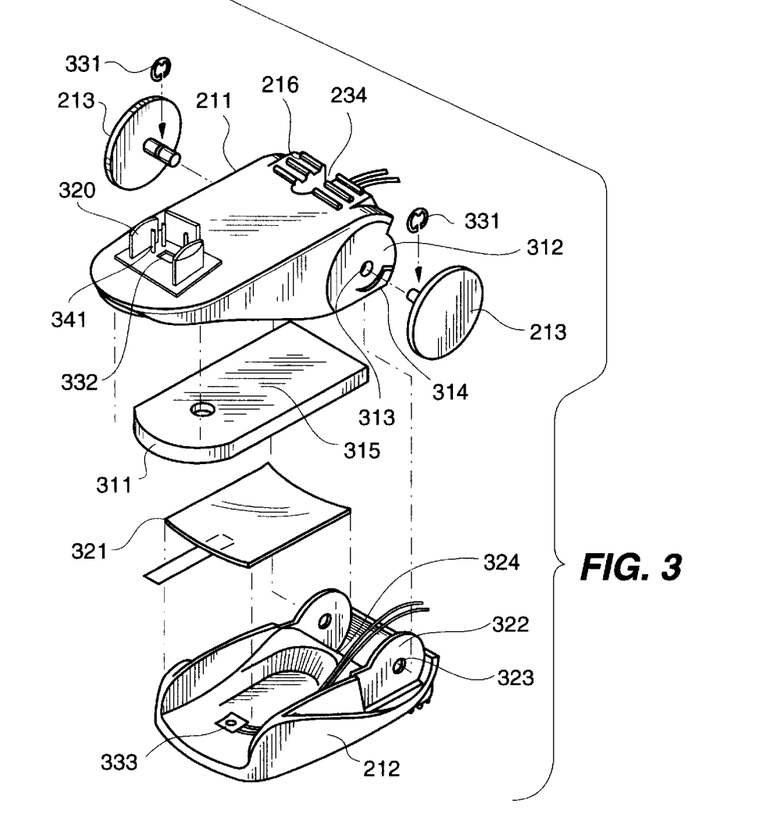

FIGS. 2 and 3 illustrate perspective and exploded views of one alternative embodiment of probe 1. This configuration is a "clip-tip" or "spring clip" probe 201 that makes use of a spring loaded pair of opposing arms 211, 212 to precisely place the patient's finger in the proper position with respect to the optical port 332 and light detector 333 elements and to place thee elements in contact with the patient's skin at the probe attachment site. The spring clip probe 201 consists of a first section 211, which is equipped with a conformable pad 311 attached to the interior surface of first section 211 and having an aperture 315 to permit light to pass from optical port 332 to the patient's finger that is placed in the spring clip probe. Also included in the first section 211 is a connector 220 for interconnecting a cable 3 to the light detector 333 included in the spring clip probe 201 and positioning the surface emitting laser devices contained in connector 220 over the optical port 332. The second section 212 of spring clip probe 201 includes light detector 333 and an adhesively coated material 321 that serves to affix the spring clip probe 201 to the patient's finger 250. The adhesive is located on the side opposite from the finger, only on material 321. The first section 211 and the second 212 section are similar in configuration and, when fitted together, function to press the optical port 332 and light detector 333 against a patient's finger 250 that is inserted between the first 211 and second 212 sections. The first 211 and second 212 sections are hingeably attached to each other and include a spring member 314 integral to the first section 211 that functions to bias the first 211 and second 212 sections together in a closed position as illustrated in FIG. 2. First 211 and second 212 sections include mating pieces that, when assembled with a pivot pin 213, function as a hinge. In particular, the first section 211 includes two areas 312, each of which has an aperture 313 formed therein to correspond to a mating aperture 323 in areas 322 on the second section 212. The first 211 and second 212 sections are aligned and interconnected by the insertion of pivot pins 213 in the respective apertures 313, 323 when oriented opposite each other such that the tissue contacting surfaces of the interior surfaces of first and second sections 211, 212 face each other. The integral spring 314 that is part of first section 211 exerts a force against the second section 212 to force the ends of the first and second housing sections 211, 212 apart, which cause the first and second housing sections 211, 212 to rotate with respect to each other around the pivot pins 313, thereby forcing the other ends of the housing together.

The interior surface of the first 211 and second 212 sections include a curved portion to substantially parallel the contours of a typical finger 250 to which the spring clip probe 201 is connected. The conformable pad 311, and adhesively coated material 321 function to compensate for topological differences between the patient's finger 250 and the curvature of the inside of the two sections 211, 212 of the spring dip probe 201. Thus, when the two sections 211, 212 of the spring clip probe 201 are dosed about a patient'finger 250, the conformable pad 311 and adhesively coated material 321 form a surface that substantially maps to the contours of the patient's finger 250. The use of the conformable pad 311 and adhesively coated material 321 and the spring mechanism 314 of the spring dip probe 201 ensures that the optical port 332 and the light detector 333 are placed in close and firm contact with the skin of the patient's finger 250. The dose contact of the optical port 332 and the light detector 333 with the patient's finger 250 is critically important since any ambient light that is received by the light detector 333 interferes with the measurement of the particular characteristics of the arterial blood that are performed by the monitoring equipment.

The interior surface of the second section 212 is also shaped to match the contours of the bottom of a finger 250 such that the interior end 324 of this recess functions as a finger stop which is designed to position the patient's finger 250 inside of the housing section 212 at a predetermined location. The height of the finger stop 324 is designed to permit a fingernail, especially a long fingernail, to pass over the top, but also to prevent the fleshy fingertip from extending beyond a selected point between the two sections 211, 212 of the spring clip probe 201. The light detector 333 is mounted in the bottom of the contoured area of second section 212 in a predetermined location.

In order to prevent the movement of the patient's finger 250 within the spring dip probe 201, the adhesively coated material 321 located in the second section 212 is implemented by means of a clear conformable material 321 that is adhesively coated on the side opposite from the finger. The conformable pad 311 adhesively affixed to the first section 211 can be manufactured of an opaque material having an aperture (hole) 315 cut therein to allow the optical port 332 affixed to the interior surface of the first section 211 of the spring clip probe 201 to transmit light through the hole 315 in the conformable pad 311 to shine on the patient's finger 250 at a predetermined location, such as near the cuticle of the finger.

The construction of the first section 211 and second section 212 of the spring clip probe 201 is such that, when dosed on the patient's finger 250, the first 211 and second 212 sections have surfaces conforming to the patient's finger 250 and close akin to a clam shell. The hingeably connected ends of the first 211 and second 212 sections of the spring clip probe 201 are cut such that in a closed position an aperture 215 is provided between the first 211 and second 212 sections. This aperture 215 is dosed when the first 211 and second 212 sections are opened to the full extent, the range of travel being determined by the size of the aperture 215. Therefore, when placed in a fully opened position the pivoting end of the first 211 and second 212 sections encounter each other, restricting the range of motion of the first 211 and second 212 sections The light detector 333 is of conventional design typically found in pulse oximeter probes. The plurality of conductors are connected to the light detector 333 and these conductors are terminated in a connector 320 located on the top surface of the first section 211 of the spring clip probe 201. This connector 320 includes a plurality of pins 341 arranged in a predetermined pattern therein, which connector 320 is located at the patient end of the spring clip probe 201 in order to provide the user with sufficient space to grasp the spring clip probe 201 for application to the patient's finger 250.

Alternative System Architecture

Figure 12:
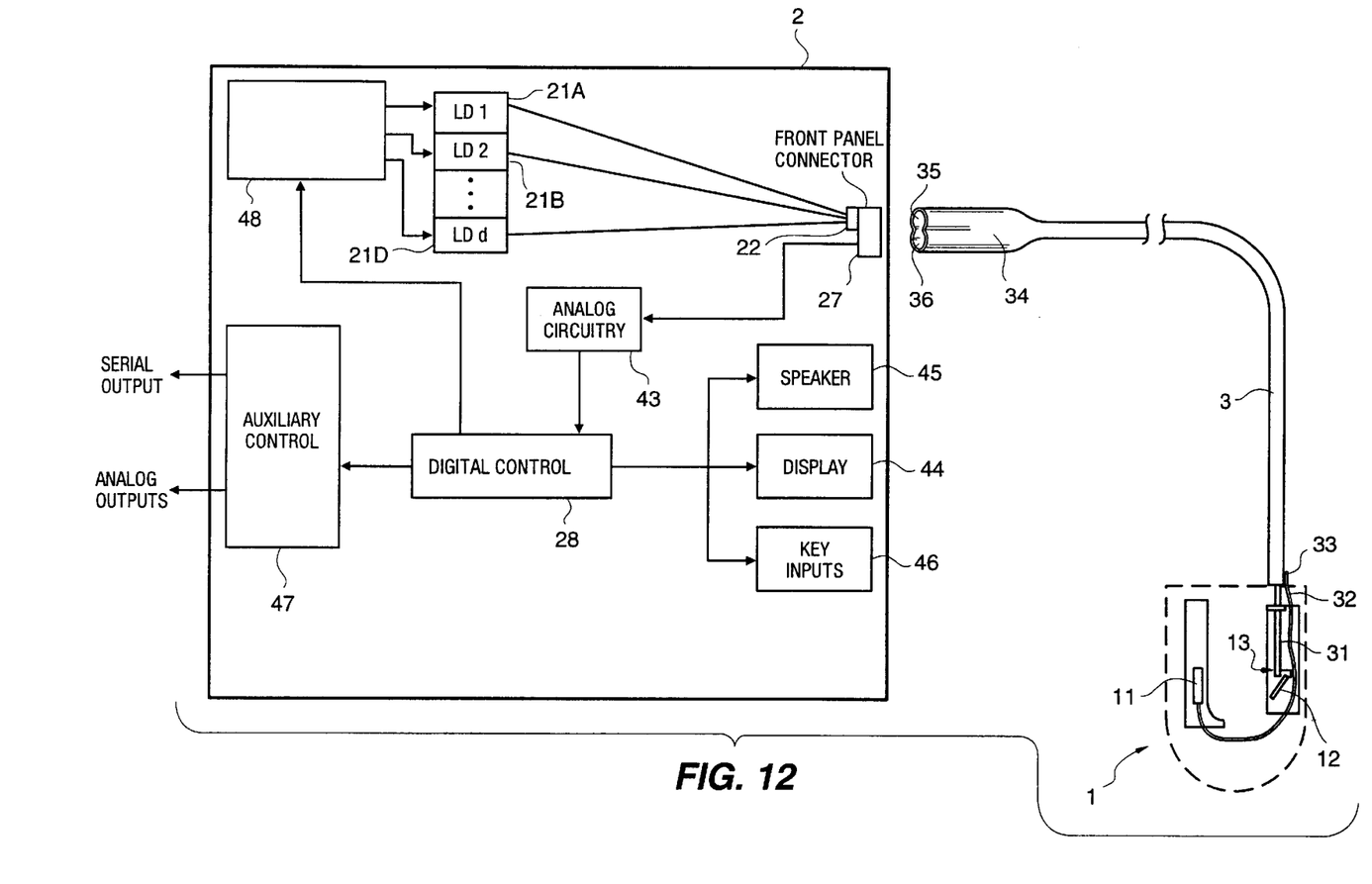
FIG. 12 illustrates the architecture of an alternative embodiment of the monitor and probe of the present invention, including a side cutaway view of the probe and a block diagram of the control and light beam generation elements of the monitor.

An alternative embodiment of the apparatus of the present invention is illustrated in FIG. 12 and consists of two primary segments: a monitor 2, and a probe 1 that is affixed to a probe attachment site on the patient. These two modules 1,2 are interconnected by a cable 3 which can be affixedly attached to and an integral part of the probe 1 or can be an element that is connectorized at both ends thereof to enable cable 3 to be disconnected from both the probe 1 and monitor 2. In the embodiment disclosed herein, cable 3 is shown as part of probe 1. The monitor 2 primarily consists of the light generation apparatus but also includes circuitry to receive the return signals produced by the reception of light that passes through the illuminated appendage as well as user interface circuitry. A plurality of laser diodes 21A–21D are noted in FIG. 12, labeled as "LD1, . . . LDd". The number of laser diodes 21A–21D (such as an array of surface emitting laser diodes) is typically equal to the number of blood analytes that are to be measured by the instrument. For standard pulse oximetry, the number of laser diodes can be as little as two, one whose light output is at a wavelength of approximately 660 nm and a second whose light output is at a wavelength of approximately 940 nm. In the system disclosed herein, four laser diodes 21A–21D are disclosed.

The wavelength of the light beams output by the laser diodes 21A–21D are affected by the operating temperature of the laser diodes 21A–21D. Since the light emitting devices, the laser diodes 21A–21D, are located in the monitor and not in the probe 1, additional control circuitry can conveniently be added to precisely regulate the temperature of the light emitting devices 21A–21D and/or compensate for variations in their temperature. In prior systems where the light emitting diodes are located in the probe module 1, these devices must be of minimalistic design since they may be disposable and to also reduce the bulk of the probe. The alternative embodiments of the invention disclosed herein can also make use of temperature feedback to regulate the operation of the system. In the case where the light emitting devices are located in the connector or in the disposable segment of the probe, the temperature sensors are co-located with the light emitting devices therein to provide feedback to the instrument to enable the measurement process to be calibrated as a function of the temperature directly measured at the light emitting devices.

The monitor 2 includes analog circuitry 43 that functions to receive and condition the electrical signals produced by the light detector 11 that is contained within the probe 1, as is well known in the art. These received signals are digitized and transmitted to digital control 28 for processing as is well known in the field to produce the required measurements. The digital control 28 outputs the computed measurements to display 44 for production of a human-readable output. A speaker 45 is typically included to enable digital control 28 to produce audible alarms to alert the user to error or danger conditions. Key inputs 46 are also typically provided to enable the user to input control information to regulate the operation of the instrument. An auxiliary control circuit 47 receives output signals from digital control 28 for transmission in serial digital and/or analog form to other elements in the medical monitoring instrument The light beams generated by the laser diodes 21A–21D are transmitted to the probe 1 via an optical fiber 31 that is part of cable 3. The optical coupler 22 shown in FIG. 12 performs the task of coupling the optical output of all the laser diodes 21A–21D to the optical fiber 31. The plurality of light beams that are produced by the plurality of laser diodes 21A–21D are coupled by the optical coupler 27 (which can be part of the front panel connector) into a single optical fiber 31 contained in the cable 3 for transmission to the probe 1. The optical coupling can be accomplished in a number of ways. A plurality of individual optical fibers (not shown) can be used to transmit the light beams produced by the laser diodes 21A–21D to the optical coupler 22 where they are interconnected into the single optical fiber 31 of cable 3. Alternatively, the light beams produced by the laser diodes 21A–21D can be coupled into a single optical fiber or directly input to the optical coupler 22 where they are interconnected into the single optical fiber 31 of cable 3.

Hybrid Cable

The pulse oximeter instrument is a connectorized system, with the cable 3 that interconnects the probe 1 with the monitor 2 being detachable from the connector 27 located on the front panel of the pulse oximeter instrument. The cable 3 is a hybrid cable, consisting of an optical fiber 31 and electrical conductor 32 combination contained within a single sheath 33.

There are a number of variations in implementation of the probe 1 that are possible with regard to the transmission of the light between the probe 1 and the monitor 2. The probe 1 can contain only passive optical elements that function to carry the light beams generated by the laser diodes 21A–21D to the probe attachment site on the patient and also return the light that is output from the patient's transilluminated appendage to a light detector (not shown) that is mounted within the monitor 2.

The cable 3 therefore includes optical fiber 31 which carries the plurality of light beams generated by the laser diodes 21A–21D as well as electrical conductors 32 which interconnect the light detector 11 of probe 1 with the processor circuit 28 in monitor 2. Connector 27 can have two adjacent or intermingled connector elements 35, 36 with a first 35 being the optical connector and a second 36 being the electrical connector.

Probe Module

The probe 1 consists of the light detector 11 and optical apparatus that applies the light beams carried by the optical fiber 31 to the patient's appendage. This optical apparatus consists of a reflective surface such as a mirror 12 mounted at an angle with respect to the end face of optical fiber 31 to reflect the incoming light beam that emanates from the end of optical fiber 31 into living tissue, such as the patient's skin, so that the reflected light beam is orthogonal to the skin surface. This configuration allows the optical fiber 31 to enter the probe 1 parallel to the long axis of the patient's finger, while applying the incident light perpendicular to the patient's skin. The mirror 12 is mounted along with optical fiber 31 in an optical mount 13 which is typically affixed to cable 3 to ensure proper positioning of the optical elements within the probe 1. The end face of the optical fiber 31 is positioned by mount 13 adjacent to the mirror 12 which reflects the light beam that emanates from the end of optical fiber 31 at a predetermined angle, such as approximately the 45° angle shown in FIG. 12, to the patient's finger. A common aluminum front surface mirror typically allows approximately 80–90% of the light at wavelengths from 635 nm to 980 nm to be reflected. The use of a gold front surface mirror improves the reflectivity to approximately 92–99%. By making the mount 13 and mirror 12 an integral part of the cable 3, the probe 1 becomes an inexpensive element, since the cost of manufacture is reduced by this simple yet accurate cable and mirror placement.

Alternatively, the optical fiber can be positioned to have its end directed at the patient's skin, thereby eliminating the need for the use of light redirection apparatus.

A lens is optionally provided to precisely direct the incident light directly on to the patient's skin. The lens can also be implemented to diffuse the light which emanates from the probe 1 or a separate diffuser element (not shown) can be incorporated to diffuse the light which emanates from probe 1. The diffusion of the light output is to ensure that the light generated by the laser diode light emitting devices 21A–21D is safe and cannot cause harmful effects if a patient were to mistakenly apply the light output from probe 1 directly into the patient's eyes.

Alternative Probe Embodiment

Figure 13:
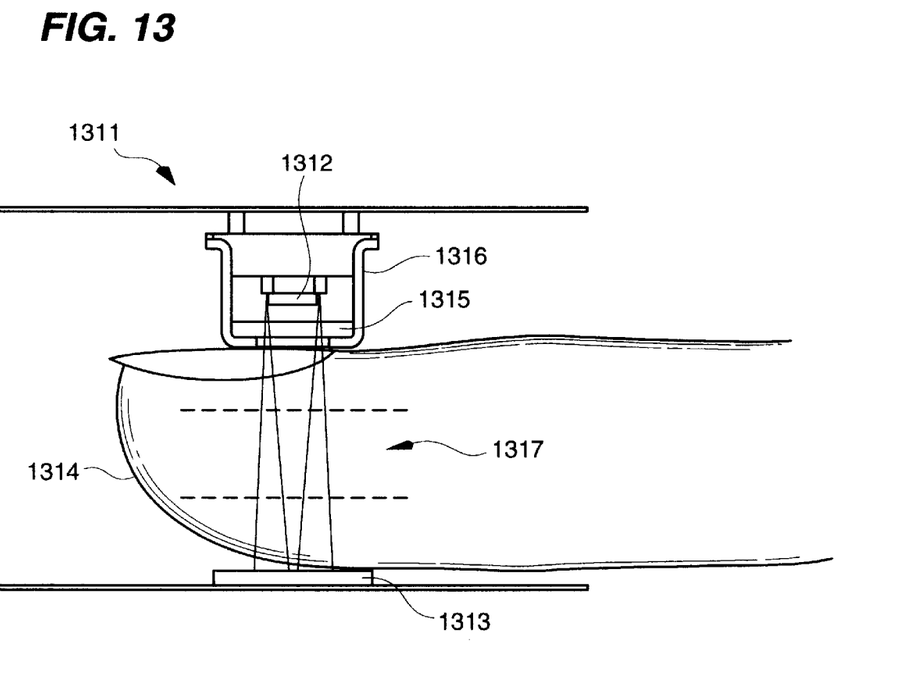
FIG. 13 illustrates the architecture of an alternate embodiment of the probe of the present invention which incorporates the light emitting devices in the disposable segment of the probe.

FIG. 13 illustrates another embodiment of the probe 1 wherein the laser diodes are an integral part of the disposable section of the probe 1. In this embodiment, the probe 1311 contains an array of the surface emitting laser diodes 1312, each of which laser diodes generates a beam of light centered about a selected wavelength. Probe 1311 also contains a light detector 1313 capable of receiving the wavelengths of light emitted by the laser diodes contained in the array 1312.The probe 1311 also contains a connector (not shown) to enable the probe 1311 to be connected to the cable 3, in a manner analogous to that shown in the other embodiments described above. The probe 1311 is positioned juxtaposed to the patient's perfused tissue (such as the finger 1314 shown in FIG. 13), and operates either in the transmission mode with the array of laser diodes 1312 on one side of the finger 1314 and the light detector 1313 on the other side of finger 1314, or in the reflectance mode where all the sensor elements 1312, 1313 are positioned on the same side of finger 1314. As can be seen from FIG. 13, the array of laser diodes 1312 includes a diffuser 1315 held in place by mount 1316. The diffusion of the light output is to ensure that the light generated by the array of laser diode light emitting devices 1312 is safe and cannot cause harmful effects if a patient were mistakenly to apply the light output from probe 1311 directly into the patient's eyes. As shown in FIG. 13, the light beams produced by the laser diodes in the array 1312 pass through the arteriolar bed 1317 located in finger 1314 and the change in the path length of these light beams as they pass through the arteriolar bed 1317 is what is measured to determine the concentration of the measured analytes. The close spacing of the laser diodes in array 1312 results in the plurality of light beams produced by the laser diodes traversing substantially a common path through the arteriolar bed 1317 which improves the accuracy of the measurements that are taken.

SUMMARY

The apparatus of the present invention makes use of a monochromatic light source, in the form of surface emitting laser devices, to produce a plurality of high intensity light beams. The light source is mounted in the probe, juxtaposed to the probe attachment site on the patient. The use of monochromatic light ensures that the transmitted wavelength is a known, improves the accuracy of the measurements and simplifies the calibration process.

It is expressly understood that the claimed invention is not to be limited to the description of the preferred embodiment but encompasses other modifications and alterations Within the scope and spirit of the inventive concept.

We claim:

1. Medical apparatus for illuminating tissue of a subject to measure light absorption of said tissue by a measurement system, wherein at least one of a patient's heart rate and oxygen saturation of arterial blood is monitored, comprising:

a plurality of surface emitting laser devices, each emitting a substantially monochromatic beam of light at a different, predetermined wavelength across a plurality of layers and through a surface mirror of a solid state structure in a direction substantially normal thereto in response to drive signals received from said measurement system, for illuminating tissue of said subject;

a light receiving means for generating a detector signal indicative of intensity of light emanating from said illuminated tissue;

means for removably attaching said plurality of surface emitting laser devices and said light receiving means to said subject, wherein each of said plurality of surface emitting laser devices is attachable to the subject in physical alignment with said light receiving means;

means for interconnecting said plurality of surface emitting laser devices and said light receiving means with said measurement system to transmit said drive signals and said detector signal therebetween.

2. The apparatus of claim 1 wherein said plurality of surface emitting laser devices comprises:

an array of surface emitting laser devices, implemented on a single substrate, for generating a plurality of beams of light, each of which is at a predetermined wavelength, which wavelengths differ from each other.

3. The apparatus of claim 1 further comprising:

wherein said means for interconnecting comprises a first connector segment in which said surface emitting laser devices are mounted; and wherein said removably attaching means comprises a second connector segment, interconnectable with said first connector segment, for receiving beams of light produced by said surface emitting laser devices mounted in said first connector segment.

4. The apparatus of claim 3 wherein said removably attaching means further comprises:

a first housing section attached to said second connector segment;

a second housing section hingeably attached to said first housing section to form a clamshell-type housing, said first and said second sections being rotatable between an open and a closed position and having an aperture in one end thereof when in said closed position to receive a member of a patient, with said first and said second housing sections both having an interior surface facing each other and an exterior surface; and wherein said first housing section has an opening formed therein for transmitting said beams of light received by said second connector segment.

5. The apparatus of claim 4 wherein said removable attaching means further comprises:

deformable means attached to said interior surface of said first housing section for compliantly conforming to said member when said first and said second housing members are in said closed position to place said deformable means in contact with said member.

6. The apparatus of claim 3 wherein said removably attaching means further comprises:

a flexible support structure for securing said received light beams in said second connector segment and said light detector in optical contact with said subject.

7. The apparatus of claim 3 wherein said first connector segment comprises:

means for mounting said plurality of surface emitting laser devices in an orientation to emit the beams of light generated by said plurality of surface emitting laser devices in a path aligned in a direct line to said tissue.

8. The apparatus of claim 7 wherein said first connector segment further comprises:

means interposed in said path between said plurality of surface emitting laser devices and said tissue for diffusing said beams of light generated by said surface emitting laser devices.

9. The apparatus of claim 3, wherein one of said first connector segment and said second connector segment comprises:

at least one heat sink to remove heat from said plurality of surface emitting laser devices.

10. The apparatus of claim 9, wherein said plurality of surface emitting laser devices comprises an array of surface emitting laser diodes, implemented on a single substrate, for generating a plurality of monochromatic beams of light, each of which is at a predetermined wavelength, which the determined wavelengths differ from each other, and wherein said at least one heat sink is electrically connected to at least one of said plurality of surface emitting laser devices.

11. The apparatus of claim 1 further comprising:

wherein said means for intercoming comprises a first connector segment; and wherein said removable attaching means comprises:

a second connector segment, interconnectable with said first connector segment, for interfacing said means for interconnecting with said removably attaching means;

means for mounting said plurality of surface emitting laser devices.

12. The apparatus of claim 11 wherein said removably attaching means further comprises:

a first housing section attached to said second connector segment;

a second housing section hingeably attached to said first housing section to form a clamshell-type housing, said first and said second sections being rotatable between an open and a closed position and having an aperture in one end thereof when in said closed position to receive a member of a patient, with said first and said second housing sections both having an interior surface facing each other and an exterior surface; and wherein said surface emitting laser device mounting means is mounted in said first housing section to illuminate tissue of said member received in said aperture.

13. The apparatus of claim 12 wherein said housing means further comprises:

deformable means attached to said interior surface of said first housing section for compliantly conforming to said member when said first and said second housing members are in said closed position to place said deformable means in contact with said member.

14. The apparatus of claim 11 wherein said removably attaching means further comprises:

a flexible support structure for securing said surface emitting laser devices and said light detector in optical contact with said subject.

15. The apparatus of claim 1, wherein said detector signal is employable by said measurement system to monitor at least one of a heart rate of the subject and oxygen saturation of arterial blood of the subject, and wherein said monochromatic beams of light corresponding with each of said plurality of surface emitting laser devices has a corresponding predetermined center wavelength, and wherein said predetermined centered wavelengths are different.

16. Apparatus for illuminating tissue of a subject to measure light absorption of said tissue by a measurement system, comprising:

a plurality of surface emitting laser devices, each producing a substantially monochromatic beam of light at a predetermined wavelength in response to drive signals received from said measurement system, for illuminating tissue of said subject, wherein said plurality of surface emitting laser devices comprises an array of surface emitting laser diodes implemented on a single substrate;

means for generating a detector signal indicative of intensity of light emanating from said illuminated tissue;

means for interconnecting said plurality of surface emitting laser devices and said light receiving means with said measurement system to transmit said drive signals and said detector signal therebetween, wherein said means for interconnecting comprises a first connector segment in which said surface emitting laser devices are mounted, and wherein said first connector segment includes at least one heat sink to remove heat from said plurality of surface emitting laser devices; and means for removably attaching said plurality of surface emitting laser devices and said light receiving means to said subject wherein said removably attaching means comprises a second connector segment, interconnectable with said first connector segment, for receiving beams of light produced by said surface emitting laser devices mounted in said first connector segment.

17. Apparatus for illuminating tissue of a subject to measure light absorption of said tissue by a measurement system, comprising:

a plurality of surface emitting laser devices, each producing a substantially monochromatic beam of light at a predetermined wavelength in response to drive signals received from said measurement system, for illuminating tissue of said subject;

means for generating a detector signal indicative of intensity of light emanating from said illuminated tissue;

means for interconnecting said plurality of surface emitting laser devices and said light receiving means with said measurement system to transmit said drive signals and said detector signal therebetween, wherein said means for interconnecting comprises a first connector segment in which said surface emitting laser devices are mounted; and means for removably attaching said plurality of surface emitting laser devices and said light receiving means to said subject wherein said removably attaching means comprises a second connector segment, interconnectable with said first connector segment, for receiving beams of light produced by said surface emitting laser devices mounted in said first connector segment.

18. The apparatus of claim 17, further comprising:

an opaque shade mounted in one of said first connector segment and said second connector segment to shield optical transmission of ambient light to said photodetector.

19. A medical apparatus for illuminating the tissue of a patient to measure light absorption of said tissue by a measurement system, wherein at least one of a patient's heart rate and oxygen saturation of arterial blood is monitored, comprising:

an array of surface emitting laser devices, defined by a single solid state structure, each emitting a substantially monochromatic beam of light at different, predetermined wavelength across a plurality of layers and through a surface mirror of said solid state structure in a direction substantially normal thereto in response to drive signals received from said measurement system, said beams illuminating said tissue of the patient;

a light receiving means for generating a detector signal indicative of intensity of light emanating from said illuminated tissue;

means for removably attaching said array of surface emitting laser devices and said light receiving means to said patient, and including a first connector segment, wherein each of said array of surface emitting laser devices is attachable to the subject in physical alignment with said light receiving means;

means for interconnecting said array of surface emitting laser devices and said light receiving means with said measurement system to transmit said drive signals and said detector signal therebetween, and including a second connector segment directly and physically interconnectable to said first connector segment, wherein said array of surface emitting laser devices is mounted to one of said first connector segment and said second connector segment in an orientation to emit the beams of light in a path in a direct line to said tissue of the patient; and a diffuser mounted in one of said first connector segment and said second connector segment and interposed in said path between said array of surface emitting laser devices and said tissue for diffusing said beams of light.

20. The apparatus of claim 19, further comprising:

at least one heat sink mounted to one of said first connector segment and said second connector segment for removing heat from said plurality of surface emitting laser devices.

* * * * *